(12) United States Patent
Stein et al.

(10) Patent No.: US 8,563,610 B2
(45) Date of Patent: Oct. 22, 2013

(54) POLYUNSATURATED FATTY ACIDS INTERACTIONS AND OXIDATIVE STRESS DISORDERS

(75) Inventors: Thomas P. Stein, Cherry Hill, NJ (US); Bernd W. Spur, Marlton, NJ (US); George H. Lambert, Belle Meade, NJ (US); Sue X. Ming, Morganville, NJ (US); Ana Rodriguez, Marlton, NJ (US)

(73) Assignees: Rutgers, The State of New Jersey, New Brunswick, NJ (US); Rowan University, Glassboro, NJ (US)

( * ) Notice: Subject to any disclaimer, the term of this patent is extended or adjusted under 35 U.S.C. 154(b) by 0 days.

(21) Appl. No.: 13/021,196

(22) Filed: Feb. 4, 2011

(65) Prior Publication Data
US 2011/0237669 A1   Sep. 29, 2011

Related U.S. Application Data

(60) Provisional application No. 61/301,287, filed on Feb. 4, 2010.

(51) Int. Cl.
*A61K 31/20* (2006.01)

(52) U.S. Cl.
USPC ......................................... 514/560

(58) Field of Classification Search
USPC ......................................... 514/560
See application file for complete search history.

(56) References Cited

U.S. PATENT DOCUMENTS 7,799,782 B2 *   9/2010   Munson et al. ............ 514/234.5

OTHER PUBLICATIONS

Cobain et al. CAS: 140: 281858, 2004.*
Ming et al., Prostaglandins, Leukotrienes and Essential Fatty acids, 2005, 73(5):379-384.*
Bazan, N.G. "Cell survival matters: docosahexaenoic acid signaling, neuroprotection and photoreceptors." Trends in Neurosciences 29: 263-271 (2006).
Bazan et al. "Brain response to injury and neurodegeneration: endogenous neuroprotective signaling." Annals of the New York Academy of Sciences 1053: 137-147 (2005).
Cracowski et al. "Vascular biology of the isoprostanes." Journal of Vascular Research 38: 93-103 (2001).
Hou et al. "Isomer-specific contractile effects of a series of synthetic f2-isoprostanes on retinal and cerebral microvasculature." Free Radical Biology & Medicine 36: 163-172 (2004).
Ming et al. "Increased excretion of a lipid peroxidation biomarker in autism." Prostaglandins Leukotrienes & Essential Fatty Acids 73: 379-384 (2005).
Montuschi et al. "Isoprostanes: markers and mediators of oxidative stress." FASEB Journal 18: 1791-1800 (2004).
Roberts et al. The biochemistry of the isoprostane, neuroprostane, and isofuran Pathways of lipid peroxidation. Brain Pathology 15: 143-148 (2005).
Serhan, C.N. "Novel eicosanoid and docosanoid mediators: resolvins, docosatrienes, and neuroprotectins." Current Opinion in Clinical Nutrition & Metabolic Care 8: 115-121 (2005).
Serhan et al. "Anti-inflammatory actions of neuroprotectin DI/protectin D1 and its natural stereoisomers: assignments of dihydroxy-containing docosatrienes." Journal of Immunology 176: 1848-1859 (2006).
Yao et al. "Altered vascular phenotype in autism: correlation with oxidative stress." Archives of Neurology 63: 1161-1164 (2006).
Yeargin-Allsopp et al. "Prevalence of autism in a US metropolitan area." JAMA 289: 49-55 (2003).

* cited by examiner

*Primary Examiner* — Rei-tsang Shiao
(74) *Attorney, Agent, or Firm* — Fox Rothschild LLP

(57) ABSTRACT

This invention relates to the identification and treatment of the effects of products derived from oxidative pathways for polyunsaturated fatty acid (PUFA) metabolism, i.e., oxidative stress in a patient by monitoring the metabolism of DHA or by administering DHA.

2 Claims, 2 Drawing Sheets

POLYUNSATURATED FATTY ACIDS INTERACTIONS AND OXIDATIVE STRESS DISORDERS

This application claims priority to U.S. provisional application 61/301,287, filed on Feb. 4, 2010, the content of which is hereby incorporated by reference in its entirety.

This invention relates to the identification and treatment of the effects of oxidative stress in a patient.

BACKGROUND OF THE INVENTION

DHA is the major brain lipid. Recent studies by several groups of investigators have shown that DHA is the parent molecule for a large number of intracellular and extracellular messengers. Chronic perturbation of the pathways regulated by these molecules could account for the subtle behavioral effects seen with neurological diseases. Oxidation of DHA gives rise to a series of non-enzymatically produced analogs of the enzymatically derived products (neuroprostanes) as shown in FIG. 1. Since the structure and chemistries of these neuroprostanes are so similar to the enzymatically-produced compounds, interference in the signal transduction pathways is likely. If the events occur in the brain, one likely outcome is behavioral changes.

Disorders in which measurements of F2-IsoPs has implicated a pathogenic role for oxidative stress include Autism, Alzheimer's disease, Asthma, Huntington's disease, Atherosclerosis, Hepatorenal syndrome, Scleroderma, Cardiac/renal ischemia/reperfusion injury, coronary angioplasty, Se and Vitamin W deficiency, organophosphate poisoning, hyperhomocysteinemia, renal transplant dysfunction, smoking, diabetes, rhabdomyolysis, bile duct obstruction, $O_2$ pulmonary toxicity in premature infants, halothane hepatotoxicity, aceminophen poisoning, age-related decline in renal function, Cr (VI) poisoning, retinopathy of the newborn, alcohol ingestion paraquat poisoning, cisplatin-induced renal dysfunction.

Autism is one of a large family of neurological diseases whose etiology is unknown. It is a neurodevelopmental disorder. Autism is believed to be genetic in origin, with the genetically susceptible being vulnerable to environmental factors. The incidence of Autism is reported to be ~1:166 and is increasing. The disease is characterized by impaired social interactions, limited verbal and nonverbal communication and repetitive and restricted behavioral patterns. Because patients with Autism exhibit a wide spectrum of symptoms and severity, it is believed that the etiology of the disease is multifactorial.

There is an unsolved problem how to sub-divide the various forms of autism based on biochemical markers rather than clinical observations. One of the reasons why there is so much interest in developing biochemical markers for neurological diseases is that biochemical markers offer the possibilities of both early diagnosis and of devising targeted therapies.

Thus there is a need to be able to track the appearance or disappearance of the non-enzymatically produced products of the oxidation of DHA, and to be able to provide for a missing analog of similar enzymatically produced analogs to prevent or treat the effects of oxidative stress.

SUMMARY OF THE INVENTION

This invention relates to the identification and treatment of the effects of products derived from oxidative pathways for polyunsaturated fatty acid (PUFA) metabolism, i.e., oxidative stress in a patient.

In one embodiment, the invention relates to methods to identify and treat autistic children, where the suspected cause of the autistic symptoms is oxidative stress.

More particularly, one embodiment of this invention relates to a method of identifying selected subgroups of autistic children using biomarkers derived from AA (arachidonic acid) and DHA (docasahexaenoic acid) and or metabolites thereof.

Another embodiment of the invention relates to the treatment of autistic patients by treating the patient with DHA and/or metabolites thereof.

Yet another embodiment relates to a method of monitoring response to treatment of an oxidative stress disorder by monitoring the amount of DHA and its metabolites in urine or blood.

DETAILED DESCRIPTION OF THE INVENTION

Figure 1:
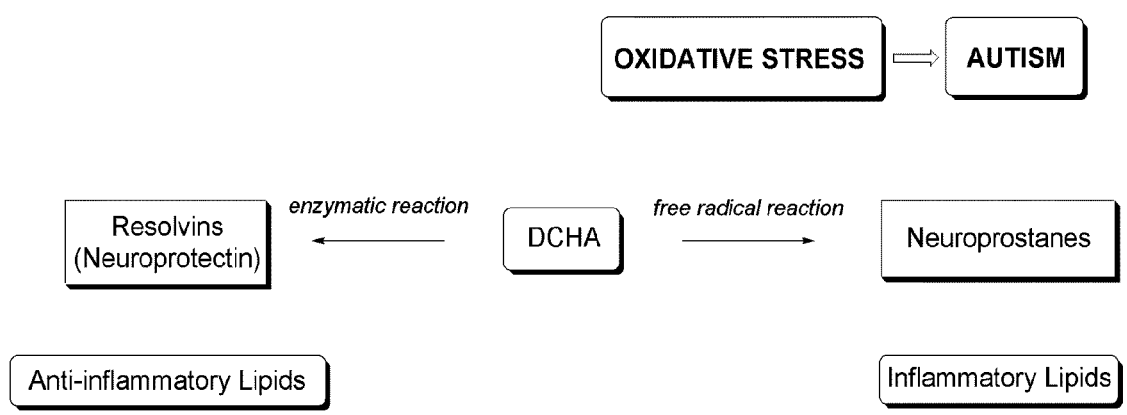
FIG. 1 shows DHA derived metabolites

This invention relates to the identification and treatment of the effects of products derived from oxidative pathways for polyunsaturated fatty acid (PUFA) metabolism, i.e., oxidative stress in a patient.

This invention relates to the diagnosis of oxidative stress related disorders as set forth above, and also including autism, asthma, neuro-developmental disorders, inflammatory bowel disorder, Parkinson's disease, Alzheimer's disease, schizophrenia, ADHD, ROP and BPD/Arthritis/periodontal disease, by assessing the amount of DHA and its metabolites in urine or blood and the kits to carry out the diagnosis.

The invention also relates to the treatment of oxidative stress related disorders as set forth above by administering DHA or a metabolite thereof to a patient experiencing the symptoms of an oxidative stress disorder.

The invention also relates to a method of monitoring response to treatment of an oxidative stress disorder by monitoring the amount of DHA and its metabolites in urine or blood.

The urinary excretion of the isoprostane $iPF_{2\alpha}$-III (8-iso-$PGF_{2\alpha}$) in children with Autism and age-matched controls has been investigated. The $F_2$ isoprostanes are derived from the auto-oxidation of arachidonic acid containing phospholipids resulting in a series of $PGF_2$ like compounds. Arachidonic acid is a naturally occurring C-20 polyunsaturated fatty acid. Excess reactive oxygen species overcome the anti-oxidant defenses and attack polyunsaturated fatty acids such as arachidonate. The resultant bicyclo-endoperoxide prostaglandin intermediates are reduced to four regioisomers, each of which can comprise 8 racemic diastereoisomers. These 64 isomers are collectively called the $PGF_{2\alpha}$, isoprostanes.

Isoprostanes and related compounds are of particular interest not only because they are markers for oxidative stress, but because they are biologically active at physiological concentrations. Some isoprostanes are potent vasoconstrictors thereby providing a plausible link between oxidative stress and pathophysiology, for example by raising blood pressure or reducing blood flow, and hence a reduced supply of nutrients to tissues. A statistically significant increase in isoprostane excretion with Autism was found. Thus it appears that there was an association between these children and oxidative stress.

Our findings of perturbation of AA metabolism suggest to us the perturbation of polyunsaturated fatty acid metabolism is not limited to AA. The cause of the perturbation is most likely due to oxidative stress—but other mechanisms—e.g. pollutants interfering with AA metabolism are also plausible.

We think a more likely is from the activity of auto-oxidation derived products from DHA rather then AA. AA and DHA are ω-3 polyunsaturated fatty acids and are commonly called 'fish oils'. The brain contains the second highest concentration of lipids in the body, after adipose tissue, with 36-60% of nervous tissue being lipids. DHA is the most abundant lipid in the brain. Just as arachidonic acid serves as the precursor for families of enzymatically produced thromboxanes, leukotrienes, prostaglandins and via auto-oxidation (isoprostanes), DHA is the precursor of a similar set of molecules.

Having the products of oxidative stress formed and acting within the brain is likely to be a much more subtle effect than raising blood pressure or generally restricting nutrient supply in genetically susceptible individuals. Autism is a subtle brain disease. The arachidonic acid hypothesis lacks the specificity of the DHA hypothesis. For assessment of oxidative damage to neural tissues, including brain, the assay of neuroprostanes may be more important than the isoprostanes.

There are three possible reasons for altered AA and or DHA metabolism:
(1) the high isoprostanes reflect an overall increase in oxidative stress;
(2) there is a genetic abnormality in the processing of AA and DHA; and
(3) pollutants trigger an abnormal response in the one or more of the AA or DHA pathways leading to isoprostanes (AA) or neuroprostanes (DHA) or resolvins (DHA) in the genetically susceptible.

Whatever the pathway, the result is an anomalous patterns of intracellular communication within the brain.

Either way, giving a pulse of excess AA or DHA and examining the urine or blood for anomalous production of AA or DHA metabolites can identify the anomalous autistic group. The importance of a biochemical marker which can be clearly linked with a biochemical pathway is that it provides a measurable target for developing and assessing treatments.

Some people have a genetically determined predisposition to be either unable to fully control the production of these analogs or the production of the enzymatically generated moieties is unduly sensitive to exogenous factors such as pollutants.

Thus one embodiment of this invention relates to a way to identify subjects with anomalous polyunsaturated fatty acid (PUFA) metabolism by taking either a baseline blood or urine specimen, giving a single dose of a mixture of DHA and EPA, collecting either a blood or urine specimen the next day to identify those subjects with a propensity to produce excessive amounts of the offspring metabolites.

If the behavioral abnormalities associated with a sub-group of autistic children is associated with altered metabolism of either AA or DHA, then:
(1) Giving a test dose of either or both should result in characteristic changes in the production of the offspring metabolites of AA and or DHA. For AA this would be isoprostanes (AA metabolism) and for DHA it would be neuroprostanes (via autoxidation) and resolvins (enzymatic).
(2) These changes should be detectable in either or both blood and urine.

The proposed diagnostic test is therefore:
(1) The collection and analysis of a baseline urine sample.
(2) The subject ingests a dose of AA, DHA, DHA+AA or DHA+EPA (eicosapentaneonoic acid).
(3) Urine is collected thereafter and analyzed for products of AA and DHA metabolism.
(4) The results of the two urine tests are compared and the changes are noted.
(5) The changes are compared to the characteristic changes of a subject having altered metabolism of either AA or DHA.
(6) A diagnosis is made.

The application as written applies to the basal state. The body continuously produces free radicals (about 3-5 g/d). It might be that endogenous defense systems can control this amount, damaging excesses only occur when production is increased. Then excessive oxidative damage to DHA and AA only occur when free radical production is increased above the basal state. Some genetically susceptible subjects will not be able to cope with this temporary surge.

These subjects can be identified by adding a free radical generating component to the test regimen. After taking the test AA/DHA mixture, a mild oxidative stress is induced. This can be done by several methods such as exercise, pharmacologically or taking an iron supplement.

With the above additions, (inducing a free radical challenge) it should be possible to identify very early those subjects with a predisposition to producing isoprostanes, neuroprostanes and anomalous amounts of neuroprostanes and resolvins. Thus there is the possibility of detecting candidates for such neurological diseases as Alzheimer's etc. very early. Early detection allows for early (prophylactic) intervention.

It is also contemplated within the invention that a subjects response to treatment of oxidative stress can be monitored by periodic urine analysis during treatment. If the biomarkers for the presence of the diagnosed disease being treated are lessened or removed, it is concluded that the treatment is working.

It is also within the scope of the invention to treat the subject with DHA in an effort to obtain a urine profile that is closer to a normal profile.

EXPERIMENTAL

Sample Collection

Single spot urine samples were collected between 10:00 AM and 4:00 PM. Urine specimens were immediately frozen on dry ice and transferred to an $-80°$ C. freezer until assay. The storage time was less than two months, which was within the range of safe storage time for the biomarkers.

Biochemical Assays

The determination of urinary 8-iso-PGF2a and 8-OHdG were performed with the laboratory investigators blinded to the identities of the subjects. We used commercially available ELISA kits for both biomarkers (8-iso-PGF2a: Oxford Biochemicals, Midland, Mich.; 8-OHdG: Genox Corporation, Baltimore, Md.). Duplicates of each sample were performed with the standards in the same 96-well plates. The results were normalized to urinary creatinine. Creatinine was measured by the picric acid method as modified for a microplate reader using a kit marketed by Sigma Chemical Co. (St. Louis, Mo.).

Statistical Analyses

Student's t-tests were used to compare differences across the various sub-groups.

Log-scale transformation was used to normalize the distribution. Where appropriate correlation and linear regression methods were employed to examine relationships among continuous variables. Contingency table analysis and associated chisquare tests were used to examine associations among qualitative variables.

Results

Figure 2:
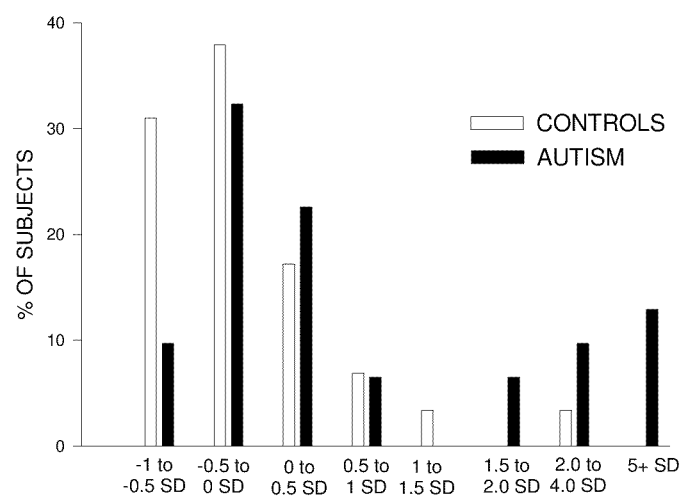
FIG. 2 shows the distribution of isoprostane excretion by autistic children follows a bimodal distribution.

The results are shown in FIG. 2.

The distribution of isoprostane excretion in children with autism was bimodal. 8-iso-PGF2α levels were significantly higher in children with autism (autism group: 32.92±1.98 ng creat-1 M; controls: 5.71±0.98 ng creat-1 M, (P=0.007).

Levels of 8-iso-PGF2α among children with autism showed a greater variability than those of controls (autism SE: 1.98, Controls SE: 0.98). On close analysis it is apparent that the increased mean was due to 23% of autistic children having isoprostane values greater than 2 SD above the mean of the control group. 13% of these children had isoprostane levels ranging from 5- to 46-fold above the control mean. The second group (77% of the children with autism) had isoprostane levels within 2 SD of the control mean. The controls show no evidence of bimodality.

References

Bazan N G. Cell survival matters: docosahexaenoic acid signaling, neuroprotection and photoreceptors. *Trends in Neurosciences* 29: 263-271, 2006.

Bazan N G, Marcheselli V L, and Cole-Edwards K. Brain response to injury and neurodegeneration: endogenous neuroprotective signaling. *Annals of the New York Academy of Sciences* 1053: 137-147, 2005.

Cracowski J L, Devillier P, Durand T, Stanke-Labesque F, and Bessard G. Vascular biology of the isoprostanes. *Journal of Vascular Research* 38: 93-103, 2001.

Hou X, Roberts L J, 2nd, Gobeil F, Jr., Taber D, Kanai K, Abran D, Brault S, Checchin D, Sennlaub F, Lachapelle P, Varma D, and Chemtob S. Isomer-specific contractile effects of a series of synthetic f2-isoprostanes on retinal and cerebral microvasculature. *Free Radical Biology & Medicine* 36: 163-172, 2004.

Ming X, Stein T P, Brimacombe M, Johnson W G, Lambert G H, and Wagner G C. Increased excretion of a lipid peroxidation biomarker in autism. *Prostaglandins Leukotrienes & Essential Fatty Acids* 73: 379-384, 2005.

Montuschi P, Barnes P J, and Roberts L J, 2nd. Isoprostanes: markers and mediators of oxidative stress. *FASEB Journal* 18: 1791-1800, 2004.

Roberts L J, 2nd, Fessel J P, and Davies S S. The biochemistry of the isoprostane, neuroprostane, and isofuran Pathways of lipid peroxidation. *Brain Pathology* 15: 143-148, 2005.

Sastry P S. Lipids of nervous tissue: composition and metabolism. *Progress in Lipid Research* 24: 69-176, 1985.

Serhan C N. Novel eicosanoid and docosanoid mediators: resolvins, docosatrienes, and neuroprotectins. *Current Opinion in Clinical Nutrition & Metabolic Care* 8: 115-121, 2005.

Serhan C N, Gotlinger K, Hong S, Lu Y, Siegelman J, Baer T, Yang R, Colgan S P, and Petasis N A. Anti-inflammatory actions of neuroprotectin D1/protectin D1 and its natural stereoisomers: assignments of dihydroxy-containing docosatrienes. *Journal of Immunology* 176: 1848-1859, 2006.

Yao Y, Walsh W J, McGinnis W R, and Pratico D. Altered vascular phenotype in autism: correlation with oxidative stress. *Archives of Neurology* 63: 1161-1164, 2006.

Yeargin-Allsopp M, Rice C, Karapurkar T, Doernberg N, Boyle C, and Murphy C. Prevalence of autism in a US metropolitan area. [see comment]. *JAMA* 289: 49-55, 2003.

The invention claimed is:

1. A method for the diagnosis of oxidative stress related disorders in a subject comprising:
   (a) collecting a sample of urine from the subject;
   (b) determining the level of polyunsaturated fatty acid metabolites selected from the group consisting of neuroprostanes and resolvins present in the urine; and
   (c) normalizing the level of polyunsaturated fatty acid metabolites present in the urine to urinary creatinine to obtain a normalized level of polyunsaturated fatty acid metabolites, wherein a normalized level of polyunsaturated fatty acid metabolites above a predetermined amount is indicative of an oxidative stress related disorder and the oxidative stress disorder is selected from the group consisting of autism, Alzheimer's disease, asthma, Huntington's disease, atherosclerosis, hepatorenal syndrome, scleroderma, cardiac/renal ischemia/reperfusion injury, coronary angioplasty, Selenium deficiency, Vitamin W deficiency, organophosphate poisoning, hyperhomocysteinemia, renal transplant dysfunction, smoking, diabetes, rhabdomyolysis, bile duct obstruction, $O_2$ pulmonary toxicity in premature infants, halothane hepatotoxicity, acetaminophen poisoning, age-related decline in renal function, Cr (VI) poisoning, retinopathy of the newborn, alcohol ingestion paraquat poisoning, cisplatin-induced renal dysfunction, neuro-developmental disorders, inflammatory bowel disorder, Parkinson's disease, schizophrenia, attention deficit hyperactivity disorder (ADHD), bronchopulmonary dysplasia (BPD), arthritis, and periodontal disease.

2. The method of claim 1, wherein the oxidative stress related disorder is Autism.

* * * * *